United States Patent [19]

Iqbal

[11] 4,367,333
[45] Jan. 4, 1983

[54] METAL COMPLEXES OF ISOINDOLINAZINES, PROCESS FOR THEIR PREPARATION AND USE

[75] Inventor: Abul Iqbal, Ettingen, Switzerland

[73] Assignee: Ciba-Geigy Corporation, Ardsley, N.Y.

[21] Appl. No.: 242,003

[22] Filed: Mar. 9, 1981

[30] Foreign Application Priority Data

Mar. 13, 1980 [CH] Switzerland .............. 1979/80

[51] Int. Cl.³ .......................................... C07D 209/14
[52] U.S. Cl. ........................ 542/417; 106/288 Q; 544/225; 546/6; 546/7; 548/105; 548/106; 548/471
[58] Field of Search ............... 542/417; 544/225; 548/105, 106; 546/6, 7; 260/326.1

[56] References Cited

U.S. PATENT DOCUMENTS 4,022,770  5/1977  L'Eplattienier .

*Primary Examiner*—Arthur P. Demers
*Attorney, Agent, or Firm*—Luther A. R. Hall

[57] ABSTRACT

1:1 metal complexes of isoindolinazines of the formula

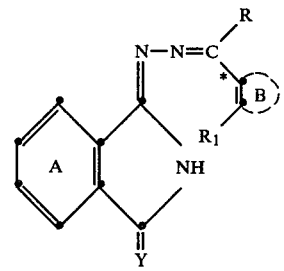

in which the ring A can be further substituted, R is a hydrogen atom or an alkyl or aryl group, B is an isocyclic or heterocyclic aromatic radical, $R_1$ is the OH or SH group and Y is a radical of the formula

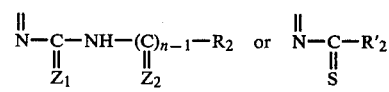

in which $Z_1$ and $Z_2$ are O or S atoms, n is the number 1 or 2, $R_2'$ is an alkyl, aryl or heteroaryl radical and $R_2$ is an alkyl, cycloalkyl, aralkyl or aryl radical or a radical of the formula

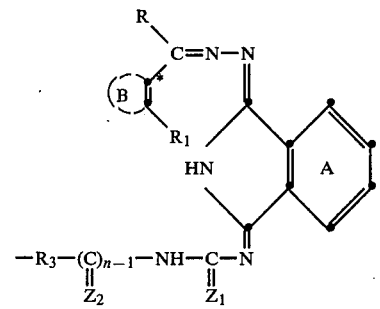

in which $R_3$ is an alkylene or arylene group.

The novel pigments color plastics and surface coatings in pure, intense orange to red shades with good fastness properties.

4 Claims, No Drawings

METAL COMPLEXES OF ISOINDOLINAZINES, PROCESS FOR THEIR PREPARATION AND USE

The invention relates to 1:1 metal complexes of isoindolinazines of the formula

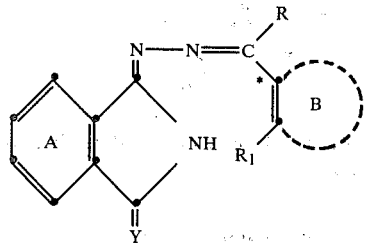

in which the ring A can be further substituted, R is a hydrogen atom or an alkyl or aryl group, B is an isocyclic or heterocyclic aromatic radical, $R_1$ is the OH or SH group and Y is a radical of the formula

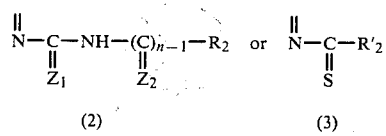

in which $Z_1$ and $Z_2$ are O or S atoms, n is the number 1 or 2, $R_2'$ is an alkyl, aryl or heteroaryl radical and $R_2$ is an alkyl, cycloalkyl, aralkyl or aryl radical or a radical of the formula

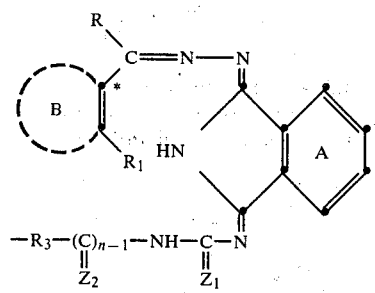

in which $R_3$ is an arylene group.

As substituents in the benzene radical A, the isoindolinonazines (sic) of the formula (1) can contain halogen atoms, for example 2-4 chlorine atoms, 1-2 alkyl or alkoxy groups having 1-4 C, a phenyl, phenoxy, nitro or benzoylamino group or an alkanoylamino group having 2-6 C, but they are preferably unsubstituted.

R is, for example, a phenyl or naphthyl radical and preferably an H atom or an alkyl group having 1-4 C, in particular the methyl group.

B is, for example, a phenylene or naphthylene radical, but especially a 5-6-membered heterocyclic ring containing an N or O atom in the β-position to the C* atom, and, if desired, N, O or S as a further heteroatom, and a fused benzene or heterocyclic ring. B is, for example, a pyrazole, pyridine, pyrimidine, quinoline or coumarin ring. $R_1$ is preferably the hydroxyl group.

An alkyl radical $R_2$ or $R_2'$ preferably has 1-4 C. Cycloalkyl $R_2$ is in particular cyclohexyl. An aryl radical $R_2$ or $R_2'$ is, for example, a naphthyl and especially a phenyl radical. A heteroaryl radical $R_2'$ is preferably a pyridine, pyridone, quinoline or coumarin radical.

Preferred metal complexes are those of the formula

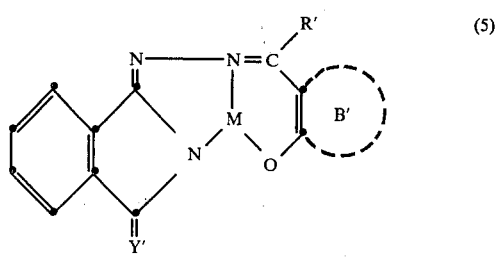

in which M is nickel or copper, R' is H or methyl, B' is a pyrazole, pyrimidine, quinoline or coumarin radical and Y' is a radical of the formula

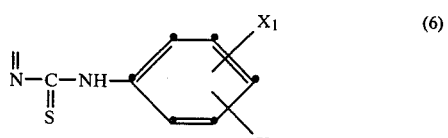

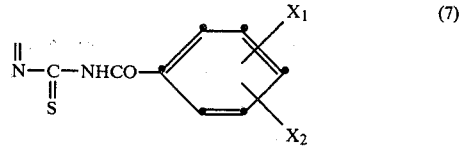

or

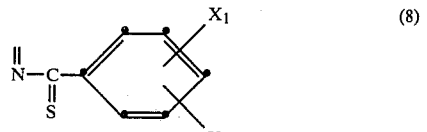

in which $X_1$ is an H, chlorine or bromine atom, a nitro, trifluoromethyl, carbamoyl or sulfamoyl group, an alkyl, alkoxy or alkylsulfamoyl group having 1-4 C, an alkanoylamino, alkylcarbamoyl or alkoxycarbonyl group having 2-6 C, or a phenoxy, phenylcarbamoyl or phenylsulfamoyl group which is unsubstituted or substituted by chlorine or bromine atoms or methyl groups, and $X_2$ is an H, chlorine or bromine atom or an alkyl or alkoxy group having 1-4 C.

The formulae (1) and (5) represent one of the various isomeric forms.

The metal complexes of the formula (1) are obtained by (a) treating an azine of the formula (1) with metal donors or (b) heating a hydrazone of the formula

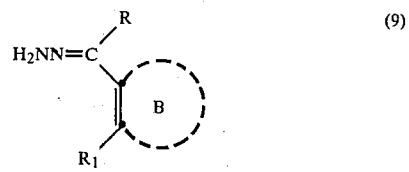

in which R, $R_1$ and B are as defined, with an isoindolinone of the formula

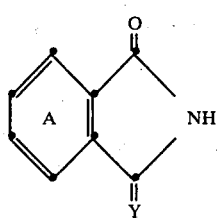

(10)

or an amino-isoindolamine of the formula

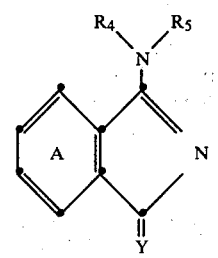

(11)

in which $R_4$ and $R_5$ are H atoms or alkyl, aryl or heteroaryl groups, or $R_4$ and $R_5$, together with the N atom, are a heterocyclic 5- or 6-membered ring, and A and Y are as defined, in the presence of metal donors, in a polar organic solvent, or (c) heating an isoindolinazine of the formula

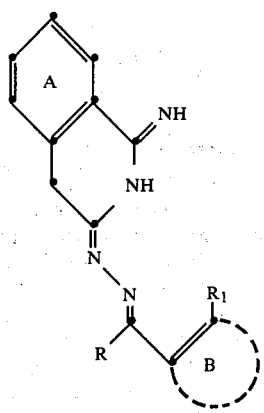

(12)

in which A, R, $R_1$ and B are as defined, with a thioamide of the formula

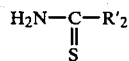

in which $R_2'$ is as defined, in the presence of metal salts, in a polar organic solvent.

The azines of the formula (1) are obtained, for example, by the process described in British Patent Specification 1,467,595, wherein a hydrazone of the formula (7) is condensed with an amino-isoinolenine (sic) of the formula (9).

The compound of the formula (11) is obtained by reacting the amino-imino-isoindolenine of the formula

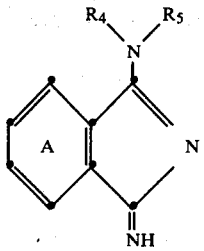

(13)

in which A, $R_4$ and $R_5$ are as defined, with a compound of the formula

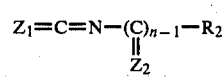

(14)

in which $R_2$, $Z_1$, $Z_2$ and n are as defined, in particular with isothiocyanates of the formulae

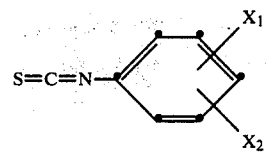

(15)

or

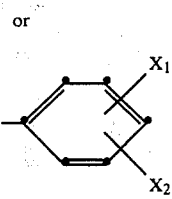

(16)

in which $X_1$ and $X_2$ are as defined.

The compound of the formula (13) is in turn obtained by reacting the amino-iminoisoindolenine of the formula

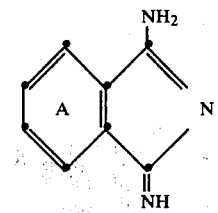

(17)

with an amine of the formula

in which $R_4$ and $R_5$ are as defined.

The compound of the formula (12) is obtained, for example, by reacting the amino-iminoisoindoline of the formula (17) with a hydrazone of the formula (9), in which A, B, R and $R_1$ are as defined.

Alkyl radicals $R_4$ and $R_5$ preferably have 1-6 C. An aryl radical $R_6$ is preferably a phenyl radical which is unsubstituted or substituted by chlorine atoms or alkyl or alkoxy groups having 1-4 C.

Examples of amino-iminoisoindolenines are those listed on page 5 of British Patent Specification No. 1,465,595. Examples of compounds of the formula (14) are: methyl isocyanate, ethyl isocyanate, n-propyl isocyanate, isopropyl isocyanate, n-butyl isocyanate, isobutyl isocyanate, cyclohexyl isocyanate, phenyl isocyanate, N-o-, m- or p-chlorophenyl isocyanate, N-o-, m- or p-methylphenyl isocyanate, N-o-, m- or p-methoxyphenyl isocyanate, N-α-naphthyl isocyanate, acetyl isocyanate, propionyl isocyanate, butyryl isocyanate, benzoyl isocyanate, methyl isothiocyanate, ethyl isothiocyanate, n-propyl isothiocyanate, isopropyl isothiocyanate, n-butyl isothiocyanate, tolyl diisothiocyanate, N-o-, m- or p-chlorobenzoyl isothiocyanate, N-o-, m- or p-methylbenzoyl isothiocyanate N-α-naphthoyl isothiocyanate, N-o-, m- or p-chlorophenyl isothiocyanate, N-o-, m- or p-methylphenyl isothiocyanate, N-o-, m- or p-methoxyphenyl isothiocyanate, N-α-naphthyl isothiocyanate, 1,4-phenyl diisocyanate, 1,4-phenyl diisothiocyanate, tolyl diisocyanate, cyclohexyl isothiocyanate and phenyl isothiocyanate.

The hydrazones of the formula (9) are obtained by known processes (sic) of reacting an oxo compound of the formula

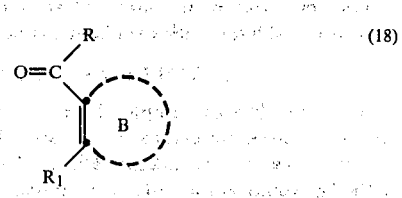
(18)

in which R, R$_1$ and B are as defined, or its imine, in particular anil, with hydrazine hydrate.

Examples of oxo compounds of the formula (18) are the aldehydes and ketones listed on pages 11 and 12 of British Patent Specification No. 1,467,595 and also 2-formyl-5,5-dimethyl-cyclohexane-1,3-dione or 1-phenyl-3-methyl-4-formyl-5-mercapto-pyrazole.

The isoindolinones of the formula (10) used as starting materials for method b are obtained by reacting the imino-isoindolinones of the formula

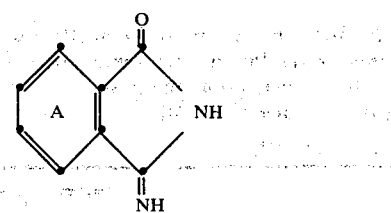

in which A is as defined, with compounds of the formula (14).

The metal donors used are preferably salts of zinc, cadmium, manganese, cobalt and iron, but especially of copper and nickel, or of mixtures of these metals. The formates, acetates or stearates of these metals are advantageously used.

The reactions take place in a polar solvent, in particular one of a hydrophilic nature, for example an amide, such as dimethylformamide, formamide, dimethylacetamide or N-methylpyrrolidone, or also dimethyl sulfoxide, acetonitrile or an alcohol, for example ethylcellosolve. It is also possible to use a mixture of polar solvents.

The reaction temperature is advantageously between 100° and 200° C.

The metal complex is isolated in the customary manner by filtration. The material on the suction filter is washed thoroughly with solvent. It is obtained in excellent yield and purity and can be used without further purification, in finely divided form, for colouring high-molecular organic material, for example cellulose ethers and esters, such as ethylcellulose, acetylcellulose and nitroecellulose, polyamides, polyurethanes or polyesters, and natural resins or synthetic resins, for example aminoplasts, in particular urea/formaldehyde and melamine/formaldehyde resins, alkyd resins, phenoplasts, polycarbonates, polyolefins, such as polystyrene, polyvinyl chloride, polyethylene, polypropylene, polyacrylonitrile and polyacrylic acid esters, thermoplastic and curable acrylic resins, rubber, casein, silicone and silicone resins, individually or in mixtures. The high-molecular compounds mentioned can be in the form of plastic masses or melts or in the form of spinning solutions, surface coatings or printing inks. Depending on the intended use, it proves advantageous to use the novel pigments as toners or in the form of preparations.

The pigments can be employed in the form in which they are obtained in the synthesis or in a lightly ground form, in which case they produce opaque final colorations. However, they can also be subjected to more intensive grinding, in which case transparent final colorations, for example intensely coloured metallic-effect coatings, are obtained.

Pastes of the pigments in surface coatings are distinguished by favourable flow properties.

The colorations obtained, for example in plastics, fibres and surface coatings, are distinguished by high colour intensity, high purity of colour shade, good dispersion of the pigments and good fastness to over-coating, migration, heat, light and weather, and also by a good gloss.

In the following examples, percentages are by weight and degrees are degrees centigrade.

EXAMPLE 1

1.09 g (0.005 mol) of 3-acetyl-4-hydroxycoumarin-hydrazone and 1.31 g (0.00525 mol) of nickel acetate.4-H$_2$O are suspended in 40 ml of ethylcellosolve. The suspension is warmed to 60° C. and 1.41 g (0.005 mol) of 1-phenylthiocarbamoyliminoisoindolin-3-one, prepared from phenyl isothiocyanate and 1-iminoisoindolin-3-one, are then added. The reaction mixture is then heated to 120° C. and stirred at the same temperature for 2 hours. The metal complex is obtained as a precipitate which is so thick that the mixture must be diluted at intervals with 40 ml of ethylcellosolve. After the reaction time of 2 hours has elapsed, the mixture is cooled to 100° C. and filtered hot. The material on the suction filter is washed with ethylcellosolve and spirit and dried overnight in vacuo at 80° C. 2.5 g (92.9% of theory) of a 1:1 nickel complex (sic) of the formula

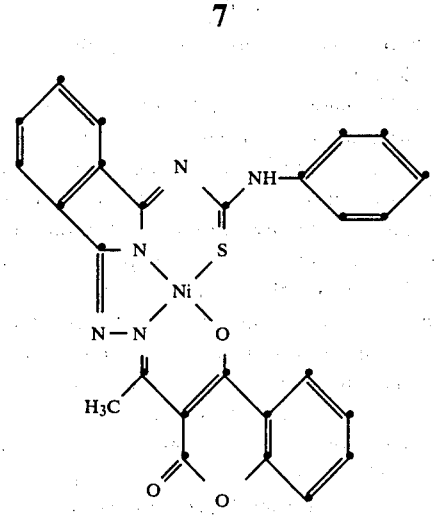

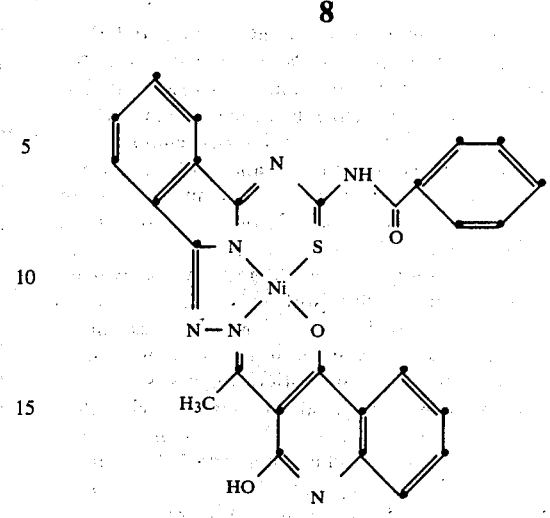

are obtained.

Elementary analysis: $C_{26}H_{17}N_5O_3SNi$, MW 538.23. Calculated C 58.02%, H 3.18%, N 13.01%, S 5.96%, Ni 10.91%. Found C 58.00%, H 3.1%, N 13.1%, S 6.2%, Ni 10.9%.

The above pigment colours plastics and surface coatings in red shades with excellent fastness properties.

EXAMPLE 2

1.09 g (0.005 mol) of 3-acetyl-2,4-dihydroxyquinoline-hydrazone and 1.31 g (0.00525 mol) of nickel acetate.4H₂O are suspended in 40 ml of ethylcellosolve, the resulting suspension is warmed to 60° C. and 1.55 g (0.005 mol) of 1-benzoylthiocarbamoylimino-3-oxo-isoindoline, prepared from benzoyl isothiocyanate and 1-imino-3-oxo-isoindoline, are then added. The reaction mixture is heated to 120° C., with stirring, and stirred at the same temperature for 2 hours. After the reaction time has elapsed, the mixture is cooled to 100° C. and filtered hot. The material on the suction filter is washed with ethylcellosolve and ethanol and dried overnight in vacuo at 80° C. In this way, 2.3 g (81% of theory) of a red metal complex of the formula are obtained.

Microanalysis: $C_{27}H_{18}N_6O_3SNi$, MW 565. Calculated 57.34% C, 3.18% H, 14.86% N, 5.66% S, 10.39% Ni. Found 57.7% C, 3.1% H, 14.9% N; 5.7% S, 10.6% Ni.

The above pigment colours plastics and surface coatings in red shades with excellent fastness properties.

EXAMPLES 3-14 (sic)

Analogously to Examples 1 and 2, further 1:1 nickel complexes are obtained by condensing the hydrazone of the oxo compounds indicated in column 2 of Table 1 with the isoindolinone of the formula

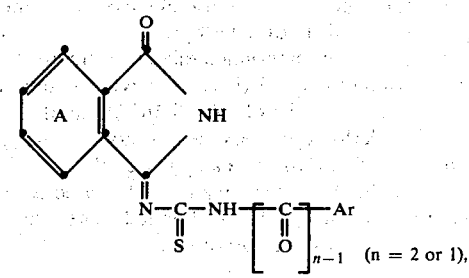

the latter having been obtained by condensing the 3-iminoisoindolinone mentioned in column 3 with the isothiocyanate compound listed in column 4. Column 5 gives the shade in PVC.

TABLE 1

| Example No. | Oxo compound | Isoindolinone | $S=C=N+C+Ar$ $\overset{\|}{O}{}_{n-1}$ (n = 2 or 1) | Shade in PVC |
|---|---|---|---|---|
| 3 | 2-phenyl-5-acetyl-4,6-dihydroxy-pyrimidine | 1-imino-isoindolin-3-one | phenyl isothiocyanate | orange |
| 4 | 3-acetyl-2,4-dihydroxy-quinoline | " | " | red |
| 5 | 5-acetyl-2,4,6-trihydroxy-pyrimidine | " | " | orange |
| 6 | 1-p-chlorophenyl-3-methyl-4-acetyl-pyrazol-5-one | " | " | red |
| 7 | 1-p-chlorophenyl-3-methyl-4-acetyl-pyrazol-5-one | " | " | red |
| 8 | 3-acetyl-2,4-dihydroxy-quinoline | " | p-chloro-benzoyl isothiocyanate | red |
| 9 | " | " | p-tolyl isothiocyanate | red |
| 10 | " | " | p-chlorophenyl isothiocyanate | red |
| 11 | 3-acetyl-4-hydroxy-coumarin | " | 3,4-dichlorophenyl | orange |

TABLE 1-continued

| Example No. | Oxo compound | Isoindolinone | $S=C=N+C+Ar$ $\overset{\|}{O}$ $n-1$ (n = 2 or 1) | Shade in PVC |
|---|---|---|---|---|
| 12 | " | " | isothiocyante p-methoxyphenyl isothiocyanate | scarlet |
| 13 | " | " | p-methoxybenzoyl isothiocyanate | orange |
| 14 | 1-phenyl-3-methyl-4-formyl-5-mercapto-pyrazole | 1-imino-isoindolin-3-one | 3-chloro-4-methyl-benzoyl isothiocyanate | red |
| 15 | 3-acetyl-4-hydroxy-coumarin | 1-imino-5,6-dichloro-isoindolin-3-one | 3-trifluoromethyl-phenyl isothiocyanate | red |

EXAMPLE 16

2.07 g (0.006 mol) of the compound of the formula

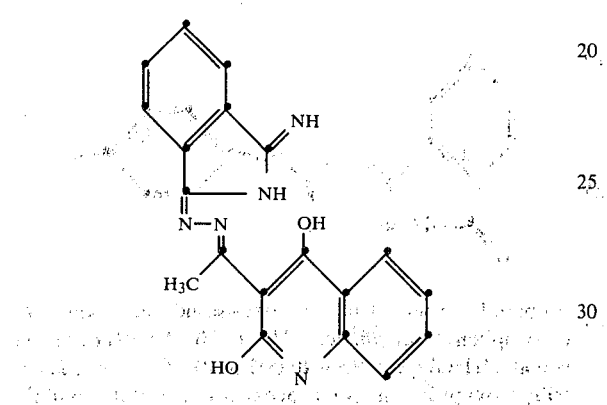

prepared from 1,3-diiminoisoindoline and 3-acetyl-2,4-dihydroxyquinoline-hydrazone, 1.5 g (0.006 mol) of nickel acetate.4H$_2$O and 0.85 g (0.006 mol) of thiobenzamide are suspended in 60 ml of dimethylformamide and the suspension is then heated to 110° C. The mixture is left to react for 1 hour at the same temperature. It is then cooled to 80° C. and filtered. The material on the suction filter is washed with dimethylformamide and ethanol and dried overnight at 80° C. in vacuo.

2.82 g (90% of theory) of the 1:1 nickel complex of the formula

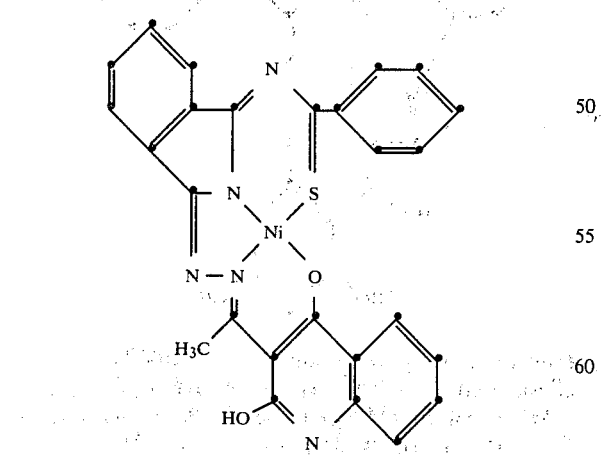

(only one of the possible isomeric or tautomeric forms has been considered) are obtained as a brown powder.

Microanalysis: C$_{26}$H$_{17}$N$_5$O$_2$SNi, molecular weight 522.2. Calculated 59.80% C, 3.28% H, 13.41% N, 6.14% S, 11.24% Ni. . . . (Sic) 59.46% C, 3.5% H, 13.82% N, 5.7% S, 11.3% Ni.

The above complex colours plastics and surface coatings in brown shades with excellent fastness properties.

EXAMPLE 17

If the procedure of Example 21 (sic) is followed, except that thioacetamide is used in place of the thiobenzamide, the 1:1 nickel complex of the following composition

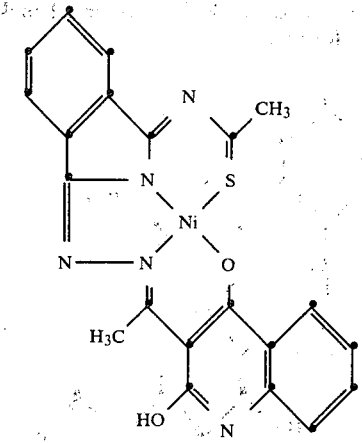

(only one of the possible isomeric or tautomeric forms has been considered) is obtained . . . (sic) reddish brown powder.

Microanalysis: C$_{21}$H$_{15}$N$_5$O$_2$SNi, molecular weight 460.2. Calculated 54.81% C, 3.29% H, 15.22% N, 6.97%, 12.76% Ni. . . . (Sic) 54.6% C, 3.5% H, 15.5% N, 6.7% S, 12.6% Ni.

The above metal complex pigment colours plastics and surface coatings in brown shades with a high level of fastness.

EXAMPLE 18

1.09 g (0.005 mol) of 3-acetyl-2,5-dihydroxyquinoline-hydrazone and 1.31 g (0.00525 mol) of nickel acetate.4H$_2$O are suspended in 100 ml of dimethylformamide, the resulting suspension is warmed to 60° C. and 1.66 g of 1-α-naphthylthiocarbamoylimino-3-oxo-isoindoline, prepared from 2-naphthyl isothiocyanate and 1-imino-3-oxo-isoindoline, are then added. The reaction mixture is heated to 120° C., with stirring, and stirred at the same temperature for 2 hours. After the reaction time has elapsed, the mixture is cooled to 100° C. and filtered hot. The material on the suction filter is washed with dimethylformamide and ethanol and dried overnight in vacuo at 80° C. In this way, 2.8 g (96% of theory) of a red metal complex of the formula

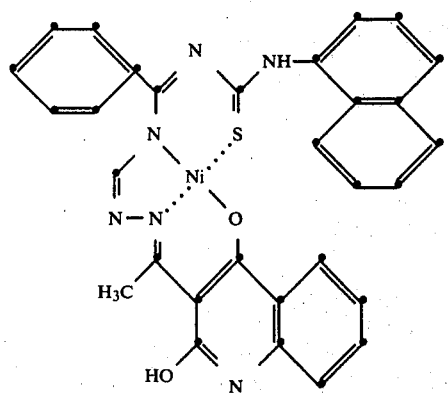

are obtained.

Microanalysis: $C_{30}H_{20}N_6O_2SNi$, MW 587. Calculated: 61.4% C, 3.4% H, 14.3% N, 5.5% S, 9.7% Ni. Found: 61.3% C 3.1% H, 14.5% N, 6.1% S, 10.0% Ni.

EXAMPLES 19–25 (sic)

Analogously to Example 18, further 1:1 nickel complexes of the formula

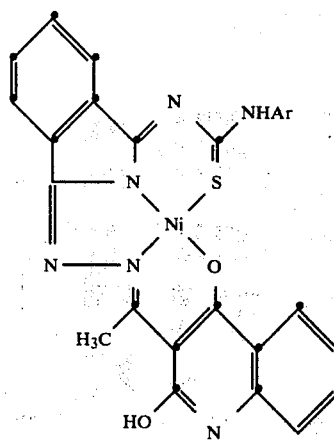

are obtained by condensing 3-acetyl-2,4-dihydroxy-quinoline-hydrazone, in the presence of nickel acetate, with the isoindolinone of the formula

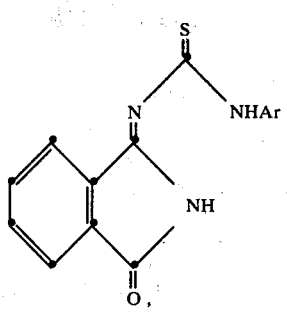

the latter having been obtained by condensing 1-imino-3-oxo-isoindoline with the isothiocyanate compounds listed in column 2. Column 3 represents the shade of the metal complexes in PVC.

| Example No. | SCN-Ar | Shade in PVC |
|---|---|---|
| 19 | m-trifluoromethyl-phenyl isothiocyanate | bluish red |
| 20 | p-nitrophenyl isothiocyanate | bluish red |
| 21 | p-phenoxy-phenyl isothiocyanate | bluish red |
| 22 | p-acetylaminophenyl isothiocyanate | scarlet |
| 23 | 4'-chlorobenzoylamino-phenyl isothiocyanate | scarlet |
| 24 | benzoyl isothiocyanate | red |

EXAMPLE 25

1.58 g (0.005 mol) of the compound of the formula

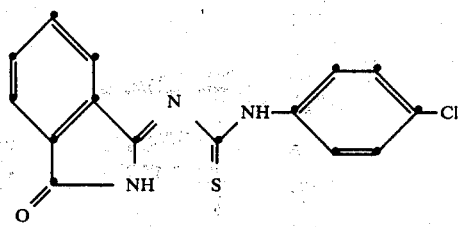

prepared from 1-imino-3-oxo-isoindoline and p-chlorophenyl isocyanate, 1.31 g (0.00525 mol) of nickel acetate.4H₂O and 0.92 g (0.005 mol) of 5-acetyl-2,4,6-trihydroxypyrimidine-hydrazone are stirred thoroughly in 70 ml of ethylcellosolve and the mixture is heated to 110° C. The mixture is stirred at the same temperature for 2½ hours and then cooled to 80° C. and filtered. The material on the suction filter is washed with ethylcellosolve and ethanol and dried overnight at 80° C. in vacuo. 2.6 g (96.5%) of the 1:1 metal complex of the following composition.

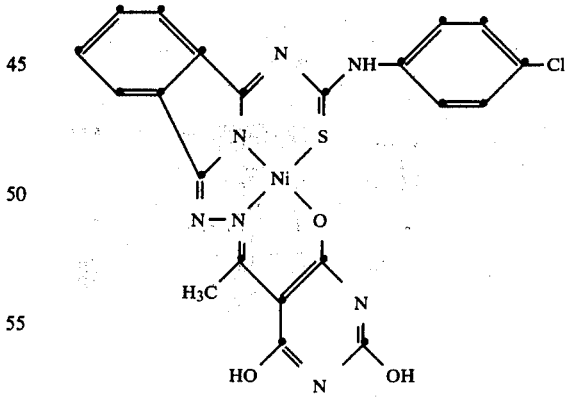

(only one of the possible tautomeric or isomeric forms is considered) are obtained as a reddish orange powder.

Microanalysis: $C_{21}H_{14}ClN_7O_3SNi$, molecular weight 538.6. Calculated: 46.83% C, 2.62% H, 18.20% N, 5.95% S 6.58% . . . (sic) 10.90% Ni. Found: 46.5% C, 2.6% H, 18.3% N, 5.9% S, 6.4% . . . (sic) 11.0% Ni.

The above metal complex colours plastics and surface coatings in pure orange shades with excellent fastness properties.

EXAMPLE 26

25 parts of the pigment prepared according to Example 2, 100 parts of finely ground sodium chloride and 30 parts of diacetone-alcohol are initially introduced into a laboratory kneader with a capacity of 250 parts by volume. The mixture is kneaded for 5 hours, with cooling, and then introduced into 4,000 parts by volume of water. The sodium chloride and diacetonealcohol dissolve and the pigment precipitates out. The suspension is filtered and the material on the suction filter is washed thoroughly with water and dried in a vacuum drying cabinet at 80°.

EXAMPLE 27

65 parts of stabilised polyvinyl chloride, 35 parts of dioctyl phthalate and 0.2 part of the pigment obtained according to Example 16 are stirred with one another and then worked on a twin-roll mill for 7 minutes at 160°. A red-coloured sheet with very good fastness to light and migration is obtained.

EXAMPLE 28

10 g of titanium dioxide and 2 g of the pigment prepared according to Example 2 are ground with 88 g of a mixture of 26.4 g of account alkyd resin, 24.0 g of melamine/formaldehyde resin (50% solids content), 8.8 g of ethylene glycol monomethyl ether and 28.8 g of Yylene (sic), for 48 hours in a ball mill.

If this surface coating is sprayed onto an aluminium foil, predried for 30 minutes at room temperature and then stoved for 30 minutes at 120° C., a red coating is obtained, which has good colour intensity and is distinguished by a very good fastness to overcoating, light and weather.

EXAMPLE 29

4 parts of the finely divided pigment according to Example 16 are stirred into 20 parts of solvent of the following composition: 50 parts of Solvesso 150 (mixture of aromatic hydrocarbons), 15 parts of butyl acetate, 5 parts of Exkin II (ketoxime-based levelling agent), 25 parts of methyl isobutyl ketone and 5 parts of silicone oil (1% in Solvesso 150).

After complete fine dispersion has been reached (in about 15–60 minutes, depending on the type of stirring), the binders are added, i.e. 48.3 parts of Baycryl L 530 (acrylic resin) (51% in xylene/butanol 3:1) and 23.7 parts of Maprenal TTX (melamine resin) (55% in butanol).

After a short period of homogenisation, the surface coating is applied by customary methods, such as spraying and dipping or, especially for the continuous coating of metal sheets, by the "coil-coating" process, and stoved (stoving: 30 minutes, 130°). The red coatings obtained are distinguished by very good levelling, high gloss and excellent fine dispersion of the pigment, and also by excellent fastness to weather.

EXAMPLE 30

If the procedure described in Example 16 is repeated, except that 2.78 parts of Staybelite Resin (HERCULES) are added to the kneading mixture, a pigment containing 10% of resin is obtained, which is distinguished by being easier to incorporate and by better dispersibility.

What is claimed is:

1. A 1:1 metal complex of an isoindolinazine of the formula

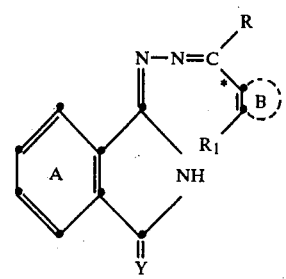

wherein ring A is unsubstituted or is substituted by two to four halogen atoms, by one or two alkyl of 1 to 4 carbon atoms, by one or two alkoxy of 1 to 4 carbon atoms, by phenyl, by phenoxy, by nitro, by benzoylamino or by alkanoylamino having 2 to 6 carbon atoms, R is hydrogen, alkyl of 1 to 4 carbon atoms, phenyl or naphthyl, B is phenylene, naphthylene or a pyrazole, pyridine, pyrimidine, quinoline or coumarin radical, $R_1$ is OH or SH, Y is a radical of the formula

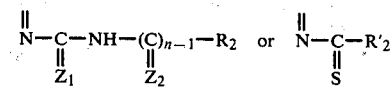

in which $Z_1$ and $Z_2$ are O or S atoms, n is the number 1 or 2, $R_2'$ is an alkyl, aryl or heteroaryl radical and $R_2$ is an alkyl, cycloalkyl, aralkyl or aryl radical or a radical of the formula

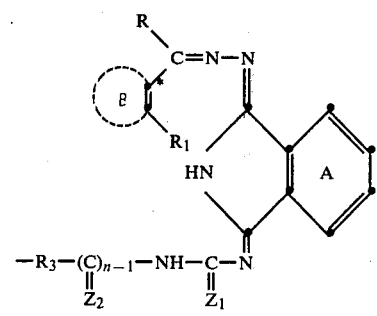

in which $R_3$ is an alkylene or arylene group, and the metal is selected from the group consisting of zinc, cadmium, manganese, cobalt, iron, copper and nickel.

2. A metal complex of the formula

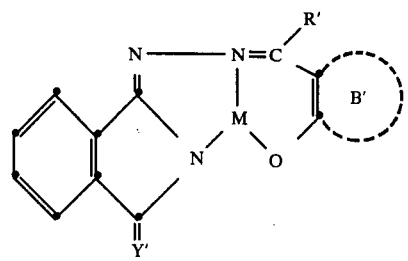

in which M is nickel or copper, R' is H or methyl, B' is a quinoline or coumarin radical and Y' is a radical of the formula

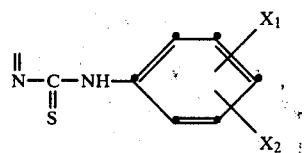 (6)

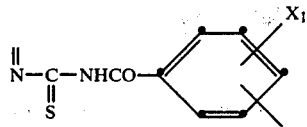 (7)

or

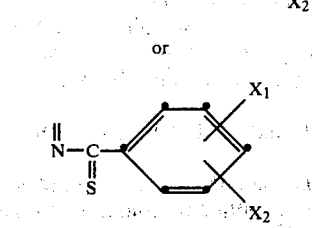

in which $X_1$ is an H, chlorine or bromine atom, a nitro, trifluoromethyl, carbamoyl or sulfamoyl group, an alkyl, alkoxy or alkylsulfamoyl group having 1–4 C atoms, an alkanoylamino, alkylcarbamoyl or alkoxycarbonyl group having 2–6 C, or a phenoxy, phenylcarbamoyl or phenylsulfamoyl group which is unsubstituted or substituted by chlorine or bromine atoms or methyl groups, and $X_2$ is an H, chlorine or bromine atom or an alkyl or alkoxy group having 1–4 C.

3. A metal complex according to claim 1 wherein B is a coumarin radical.

4. A nickel complex according to claim 2 which has the formula

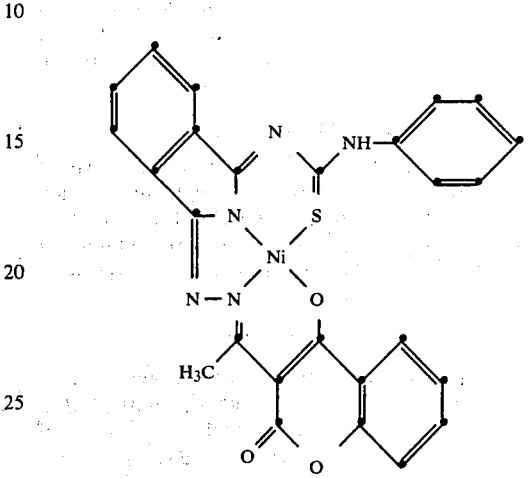

or is an isomer or tautomer thereof.

* * * * *